(12) United States Patent
Galindro et al.

(10) Patent No.: US 7,541,494 B2
(45) Date of Patent: Jun. 2, 2009

(54) PROCESS FOR THE MANUFACTURE OF IOHEXOL

(75) Inventors: José Galindro, Lisbon (PT); Susana Marto, Costa da Caparica (PT); João Bandarra, Loures (PT); William Heggie, Palmela (PT)

(73) Assignee: Hovione Inter Ltd., Lucerne (CH)

( * ) Notice: Subject to any disclaimer, the term of this patent is extended or adjusted under 35 U.S.C. 154(b) by 0 days.

(21) Appl. No.: 12/094,589

(22) PCT Filed: Mar. 3, 2006

(86) PCT No.: PCT/GB2006/000768

§ 371 (c)(1),
(2), (4) Date: Aug. 11, 2008

(87) PCT Pub. No.: WO2007/060380

PCT Pub. Date: May 31, 2007

(65) Prior Publication Data

US 2009/0048463 A1     Feb. 19, 2009

(30) Foreign Application Priority Data

Nov. 24, 2005   (PT) ...................................... 103391

(51) Int. Cl.
*C07C 233/65*   (2006.01)

(52) U.S. Cl. ................................... 564/153; 424/9.452

(58) Field of Classification Search .............. 424/9.452; 564/153

See application file for complete search history.

(56) References Cited

U.S. PATENT DOCUMENTS

| 4,250,113 A | 2/1981 | Nordal et al. |
| 6,469,208 B1 | 10/2002 | Villax et al. |
| 6,897,339 B2 | 5/2005 | Turchetta et al. |

FOREIGN PATENT DOCUMENTS

| WO | 9808804 A1 | 3/1998 |
| WO | 2005003080 A1 | 1/2005 |

OTHER PUBLICATIONS

Foreign communication from the priority application—International Search Report and Written Opinion, PCT/GB2006/000768, May 3, 2006, 8 pages.

*Primary Examiner*—Shailendra Kumar
(74) *Attorney, Agent, or Firm*—Conley Rose, P.C.; Rodney B. Carroll

(57) ABSTRACT

A process for the production of iohexol comprises alkylating 5-Acetamido-N,N'-bis(2,3-dihydroxypropyl)-2,4,6-triiodo-isophthalamide using 2(2-methoxy-ethoxy)-ethanol as solvent in the presence of a base, and optionally isolating crude iohexol from the reaction mixture. Preferably, the alkylating agent is 1-chloro-2,3 propanediol and the base is an alkali metal hydroxide such as sodium hydroxide or potassium hydroxide.

17 Claims, No Drawings

PROCESS FOR THE MANUFACTURE OF IOHEXOL

This application is a 371 of PCT/GB2006/000768, filed Mar, 3, 2006.

The present invention is related to a process for the manufacture of iohexol, 5-[N-(2,3-dihydroxypropyl)-acetamido]-N,N'-bis(2,3-dihydroxypropyl)2,4,6-triiodoisophtalamide.

Iohexol is one of the most often used non-ionic iodinated X-ray contrast agents. In the manufacture of iohexol a multi-step synthesis is involved.

Several methods have been disclosed in the literature for the synthesis of iohexol. Given that the dose of iohexol, which is administered over a short period of time, can be up to, or even more than 100 g the use of solvents with low toxicity in the last step is crucial as it is to be expected that some residual solvent, even at low levels, always remains in the final product. From an industrial point of view both easily available and solvents of low toxicity are preferable when carrying out the last step of the process. An efficient and industrially viable purification and crystallization step is required not only to obtain a product wherein the impurities are kept at minimal levels but also where the levels of residual solvents is also very low. The use of 2-methoxyethanol and mixtures of 2-methoxyethanol/isopropanol and a solvent chosen from a C1-C5-monoalkylether of a C3-C10 alkylene-glycol are respectively disclosed in WO 98/08804 and WO 2005/003080 as reaction solvents in which the N-alkylation of the nitrogen atom of 5-acetamido-N,N'-bis(2,3-dihydroxypropyl)-2,4,6-triiodoisophthalamide is carried out.

According to procedures defined in the prior art, after complete reaction, crude iohexol is isolated by removal of the high boiling solvent such as 2-methoxyethanol, usually by distillation, followed by purifying the crude product by known methods and finally, crystallizing from a suitable alcohol as described in U.S. Pat. No. 6,469,208 and references cited therein, or from mixtures of solvents including the high boiling reaction solvents and alcohols such as methanol as disclosed in WO2005/003080 or 1-methoxy-2-propanol either alone or mixed with other solvents such as isopropanol as claimed in U.S. Pat. No. 6,897,339.

Industrially, the removal of high boiling solvents is a time and energy consuming operation. There is also an increased risk that the product will degrade if high temperatures are involved during this concentration step. In addition, from an environmental point of view, both the aqueous and organic streams of the process have to be disposed-of, increasing costs considerably.

The use of a more convenient solvent in the reaction step, which is easily eliminated, and which allows crude iohexol to be isolated in a simple fashion, preferably by precipitation of the reaction mixture with a non-solvent that is easily removable by a subsequent treatment is to be preferred.

According to the procedure of the present invention, the crude iohexol is isolated by precipitation. The remainder of the process steps, up to the final crystallization are essentially aqueous, which is both industrially and environmental more desirable. A further advantage is that the overall cost of the manufacturing process is reduced.

Having appreciated the above needs, we have now found that, surprisingly, 2-(2-methoxyethoxy)ethanol meets the requirements as outlined above.

Accordingly, the present invention provides a process for the production of iohexol which process comprises alkylating 5-Acetamido-N,N'-bis(2,3-dihydroxypropyl)-2,4,6-triiodo-isophthalamide using 2(2-methoxy-ethoxy)ethanol as solvent in the presence of a base, and optionally isolating crude iohexol from the reaction mixture.

When 2-(2-methoxyethoxy)ethanol is used in conjunction with a lower boiling non-solvent such as acetone, 4-methyl-pentan-2-one, 2-methylpropan-1-ol, propan-2-ol or isopropyl acetate in the isolation step, the crude iohexol can be precipitated directly from the reaction mixture. The 2-(2-methoxyethoxy)ethanol, can then be efficiently removed from the solid by filtration followed by washing of the filter cake with the low boiling solvent chosen. The solvents known in the prior art such as the structurally similar 2-methoxyethanol cannot be used in this procedure due to the formation of gummy solids. Thus the crude iohexol is filtered, washed with the non-solvent to remove the remaining of the reaction solvent and other impurities from the reaction. An added advantage is that the yield of recovered iohexol is almost quantitative. Thereafter, the filter cake is dissolved in water and the salts formed during the reaction are removed by the use of ion exchange resins.

After further purification, if necessary, the water is removed and the iohexol can be crystallized from ethanol using the conditions disclosed in U.S. Pat. No. 6,469,208.

A further unexpected advantage that the use of 2-(2-methoxyethoxy)ethanol bestows on the process is that it is surprisingly highly efficient as reaction solvent for the production of iohexol. Some of the benefits are: the reaction can be carried out at high concentration; the reaction can be carried out at lower temperatures thus reducing decomposition and formation of by-products; less solvent is necessary and therefore waste streams are significantly reduced. 2-(2-Methoxyethoxy)ethanol is an excellent solvent for basified 5-acetamido-N,N'-bis(2,3-dihydroxypropyl)-2,4,6-triiodoisophthalamide, dissolution is achieved after one to two hours of stirring in the conditions described hereafter. This is an important improvement over the prior art because the method of the present invention reduces the time that 5-acetamido-N,N'-bis(2,3-dihydroxypropyl)-2,4,6-triiodoisophthalamide is in contact with base at high temperatures before the addition of the alkylation agent, thus reducing the potential formation of impurities. Typically, in the prior art (see the examples described in WO 2005/003080), the 5-acetamido-N,N'-bis(2,3-dihydroxypropyl)-2,4,6-triiodoisophthalamide is stirred at 45° C. overnight.

This prolonged initial phase of the reaction implies longer processing times.

The process of the present invention requires much shorter times and the typical end point for complete reaction at which time the reaction is quenched takes less than 24 hours. This results in a reduction of the impurities resulting from O-alkylation reactions and other miscellaneous process impurities.

In the process of the present invention, 5-acetamido-N,N'-bis(2,3-dihydroxypropyl)-2,4,6-triiodoisophthalamide is allowed to react with an alkylating agent, which is preferably 3-chloropropane-1,2-diol, in 2-(2-methoxyethoxy)ethanol (the reaction solvent) preferably at a concentration of 25% to 40% (w/w) relative to the solvent, suitably at 25° C. to 33° C. for preferably 18 to 24 hours. Hence, 5-acetamido-N,N'-bis(2,3-dihydroxypropyl)-2,4,6-triiodoisophthalamide is suspended in 2-(2-methoxyethoxy)ethanol and a base, which is preferably a concentrated aqueous solution of an alkali metal hydroxide, more preferably sodium hydroxide, suitably at a temperature of from 40 to 60° C., preferably from 50 to 55° C., is added to cause dissolution. The concentration of the base, for example, sodium hydroxide solution, is preferably between 59 to 73% weight/volume of water, more preferably between 65 to 67%. Dissolution is typically achieved after about one to two hours of stirring at temperatures between 40 to 60° C. After preferably cooling to a temperature of from 25 to 35° C. the alkylating agent, for example 3-chloropropane-1,2-diol, is added and the reaction is allowed to proceed, suitably at a temperature of from 25 to 35° C., preferably from 29 to 31° C. until the desired level of conversion is achieved.

After complete reaction the pH of the mixture is typically adjusted to below 7, preferably 5 to 6 by the addition a suitable acid, for example hydrochloric acid or acetic acid, and preferably the water content reduced to below 1% (w/w) by vacuum or azeotropic distillation of a small portion of the solvent. The remainder of the solvent is preferably separated from the iohexol by precipitation of the product as a solid in the following way: the mixture is added to warmed non-solvent, for example acetone, at a temperature of from 45 to 60° C., preferably 52 to 56° C. The iohexol precipitates giving a good dispersion of the solids in the mixture. The suspension is cooled preferably for not less than one hour to a temperature of from 0° C. to 25° C., preferably at a temperature of from 0 to 5° C. and typically stirred for not less than half an hour with the objective of maximize the yield. The solids are separated by filtration and washed with the non-solvent, which can be previously cooled before this wash.

Another important advantage of the present invention is that the non-solvent can be recovered from the mother liquor, as it is easily separated from the higher boiling 2-(2-methoxyethoxy)ethanol by simple distillation, and reutilized in the process, thus diminishing environmental impact by reduction of the volume of organic waste and reducing industrial costs.

Thereafter, the crude iohexol can be further purified by the methods described in the prior art, for example in U.S. Pat. No. 6,469,208.

The process of the invention is best clarified by the description of the non-limiting examples described hereafter.

EXAMPLE 1

5-Acetamido-N,N'-bis(2,3-dihydroxypropyl)-2,4,6-triiodoisophtalamide (200 g; 0.27 moles) was added to 2-(2-methoxy-ethoxy)ethanol (300 ml) and heated to 44-46° C. At this temperature a previously prepared solution of sodium hydroxide (15.0 g) and water (18.3 ml) was added and the mixture was heated to 50-52° C. until dissolution. The solution was cooled to 29° C.-31° C. and 1-chloro-2,3-propanodiol (37.2 g) was added to the solution. The temperature was set at 29-31° C. and stirred until complete reaction (21 h). Quenching was carried out by the addition of concentrated hydrochloric acid until a pH between 4 to 5. Part of the solvent was distilled under vacuum until a value of water content by Karl-Fischer of 0.04% w/w in the reaction mixture.

The solution was slowly added to acetone (1600 ml) previously heated to 55° C. The suspension was cooled to a temperature between 0° C. to 5° C., filtered under nitrogen and the solid suspended into acetone (800 ml) at 0° C., filtered under nitrogen, washed with acetone (200 ml) and dried at 60° C. 236.6 g of crude iohexol were obtained with a content of 2-(2-methoxy-ethoxy)ethanol of 2547 ppm.

EXAMPLE 2

5-Acetamido-N,N'-bis(2,3-dihydroxypropyl)-2,4,6-triiodoisophtalamide (100 g) was added to 2-(2-methoxy-ethoxy)ethanol (125 ml) and heated to 44-46° C. At this temperature a previously prepared solution of sodium hydroxide (7.48 g) and water (9.12 ml) was added and the mixture was heated to 50-52° C. until dissolution. 25 ml of 2-(2-methoxy-ethoxy)ethanol were used to wash the equipment used to prepare the sodium hydroxide solution and added to the reaction mixture. After about one hour at 52° C. the reaction mixture was heated to 60° C. and held at this temperature for 20 minutes after which dissolution was observed. The solution was cooled to 29° C.-31° C. and 1-chloro-2,3-propanodiol (18.8 g) was added to the reaction mixture. The temperature was set at 29-31° C. and stirred until complete reaction (21 h). Quenching was carried out by the addition of 1.72 ml of concentrated hydrochloric acid. Part of the solvent was distilled under vacuum until a value of water content by Karl-Fischer of 0.04% w/w in the reaction mixture.

The solution was slowly added to 800 ml of recovered acetone previously heated to 56° C. The suspension was cooled to a temperature between 0° C. to 5° C., stirred during 1 hour at this temperature, filtered under nitrogen and the solid suspended into recovered acetone (400 ml) at 0° C., filtered under nitrogen, washed with acetone (100 ml) and dried at 60° C. 113.4 g of crude iohexol were obtained with a content of 2-(2-methoxy-ethoxy)ethanol of 3569 ppm.

EXAMPLE 3

100 g of 5-Acetamido-N,N'-bis(2,3-dihydroxypropyl)-2,4,6-triiodoisophtalamide where converted to iohexol in the experimental conditions described in example 2. After complete conversion the reaction was quenched by the addition of 0.8 ml of glacial acetic acid.

One half of the reaction mixture was heated to 60 to 70° C. and 12 ml of solvent were distilled under vacuum. The water content after distillation was 0.16% (w/w). The warm iohexol solution in 2-(2-methoxy-ethoxy)ethanol was slowly added to 400 ml of acetone previously heated to a temperature between 50° C. to 55° C. at stirred during 30 minutes at the same temperature. The suspension was cooled to a temperature between 0° C. to 5° C., filtered under nitrogen and the solid suspended in acetone (200 ml) after which it was stored overnight at room temperature. The suspension was cooled to a temperature between 0° C. to 5° C. and stirred during 30 minutes at this temperature. The solids where collected by filtration, washed with acetone (124 ml) and dried at 60° C. 56.16 g of crude iohexol were obtained with a content of 2-(2-methoxy-ethoxy)ethanol of 6215 ppm.

EXAMPLE 4

The water content of a crude iohexol solution corresponding to 25 g of 5-Acetamido-N,N'-bis(2,3-dihydroxypropyl)-2,4,6-triiodoisophtalamide (previously converted to crude iohexol in the conditions described in example 2, wherein the solvent was used in a ratio of 3 ml per gram of starting 5-acetamido-N,N'-bis(2,3-dihydroxypropyl)-2,4,6-triiodoisophthalamide) was reduced to not more than 0.4% by azeotropic distillation. After, the reaction mixture was added to 2-methylpropan-1-ol (200 ml) previously heated to 75° C. The obtained suspension was cooled to room temperature. The solids where collected by filtration, washed with 2-methylpropan-1-ol (75 ml) and dried at 60° C. 23.45 g of crude iohexol were obtained with a content of 2-(2-methoxy-ethoxy)ethanol of 2675 ppm.

EXAMPLE 5

A solution of crude iohexol (15% w/w) in water, containing 88.26 g of iohexol was sequentially passed through a set of acid and basic ion exchange resins to remove the salts and other process impurities. The water was removed by distillation and the solvent replaced by ethanol. The water content was further reduced by azeotropic distillation and the iohexol then crystallized from ethanol (354 ml) at 75° C. with a water content below 1% w/w in the crystallization mixture. The iohexol so obtained was washed with ethanol (268 ml) at 75° C. stirred for 2 hours at this temperature, the suspension was cooled to below 5° C., filtered and washed with absolute ethanol. After drying at 60° C. 62.38 g of iohexol was obtained with purity by HPLC of 99.2% in area with 0.4% of O-alkylation impurities. The content by HPLC of the largest single unknown impurity present in the final product is 0.03% and the content of 2-(2-methoxy-ethoxy)ethanol 77 ppm.

EXAMPLE 6

A solution of crude iohexol (11% w/w) in water, containing 35.75 g of iohexol (previously separated from the reaction mixture by precipitation with propan-2-ol and dried in the conditions example 2) was sequentially passed through a set of acid and basic ion exchange resins to remove the salts and other process impurities. iohexol was isolated in the experimental conditions described in Example 5. The water was removed by distillation and the solvent replaced by ethanol. The water content was further reduced by azeotropic distillation and the iohexol finally crystallized from ethanol (200 ml) at 75° C. with a water content below 1% w/w in the crystallization mixture. The iohexol so obtained was washed with ethanol (185 ml) at 75° C. and stirred for 4 hours at this temperature, the suspension was cooled to below 5° C., filtered and washed with absolute ethanol (50 ml). After drying at 60° C., 22.37 g of iohexol was obtained with purity by HPLC of 99.6% in area with 0.22% of O-alkylation impurities. The content by HPLC of the largest single unknown impurity present in the final product is 0.03% and the content of 2-(2-methoxy-ethoxy)ethanol 51 ppm.

The invention claimed is:

1. A process for the production of iohexol which process comprises alkylating 5-Acetamido-N,N'-bis(2,3-dihydroxypropyl)-2,4,6-triiodoisophthalamide using 2(2-methoxyethoxy)-ethanol as solvent in the presence of a base, and optionally isolating crude iohexol from the reaction mixture.

2. The process according to claim 1 wherein the alkylating agent is 1-chloro-2,3 propanediol.

3. The process according to claim 1 wherein the solvent is used in a ratio of from 1 ml to 3 ml per gram of 5-acetamido-N,N'-bis(2,3-dihydroxypropyl) -2,4,6-triiodoisophthalamide.

4. The process according to claim 1, where the base is an alkali metal hydroxide, such as sodium hydroxide or potassium hydroxide.

5. The process according to claim 1 wherein an aqueous solution of the base is added to a suspension of 5-acetamido-N,N'-bis(2,3-dihydroxypropyl)-2,4,6-triiodoisophthalamide in the solvent.

6. The process according to any one of claim 1 wherein the concentration of the base is 59 to 73%, expressed as weight per volume.

7. The process according to claim wherein the quantity of the base added is from 71 mg to 78.5 mg per gram of 5-acetamido-N,N'-bis(2,3-dihydroxypropyl)-2,4,6-triiodoisophthalamide.

8. The process according to claim 5, wherein the temperature of the reaction mixture is set at from 40 to 60° C. and stirred until dissolution is achieved.

9. The process according to claim 1 where the alkylation reaction is carried out at 25° C. to 35° C.

10. The process according to claim 1 where the pH of the reaction mixture after complete reaction is adjusted to from 5 to 7 with an acid.

11. The process according to claim 10 wherein the acid is hydrochloric acid or acetic acid.

12. The process according to claim 10 wherein the water content is adjusted to below 1% by vacuum or azeotropic distillation.

13. The process according to claim 1 further comprising the isolation of crude iohexol by precipitation with a non-solvent.

14. The process according to claim 13 where the said non-solvent comprises acetone, 2-methylpropan-1-ol, or propan-2-ol.

15. The process according to claim 13 wherein the reaction mixture is added to the non-solvent at a temperature of from 50° C. to 75° C.

16. The process according to claim 13, wherein crude iohexol is separated from the solvent by filtration and washing with the non-solvent.

17. The process according to claim 13, further comprising recovering the non-solvent by distillation and re-using it in the process.

* * * * *

UNITED STATES PATENT AND TRADEMARK OFFICE
CERTIFICATE OF CORRECTION

PATENT NO.        : 7,541,494 B2
APPLICATION NO.   : 12/094589
DATED             : June 2, 2009
INVENTOR(S)       : José Galindro et al.

It is certified that error appears in the above-identified patent and that said Letters Patent is hereby corrected as shown below:

In Column 6, Claim 6, Line 8, delete "any one of"

In Column 6, Claim 7, Line 11, insert "1" between "claim" and "wherein"

Signed and Sealed this

Fourth Day of August, 2009

JOHN DOLL
*Acting Director of the United States Patent and Trademark Office*